(12) United States Patent
Ye et al.

(10) Patent No.: US 11,892,397 B2
(45) Date of Patent: Feb. 6, 2024

(54) ENDOTOXIN TESTING ASSAY AND METHOD OF SAME

(71) Applicant: BOARD OF REGENTS, THE UNIVERSITY OF TEXAS SYSTEM, Austin, TX (US)

(72) Inventors: Jing Yong Ye, San Antonio, TX (US); Jonathan D. Scudder, San Antonio, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 17/316,467

(22) Filed: May 10, 2021

(65) Prior Publication Data

US 2021/0262924 A1 Aug. 26, 2021

Related U.S. Application Data

(63) Continuation-in-part of application No. 16/162,261, filed on Oct. 16, 2018, now Pat. No. 11,099,189.
(Continued)

(51) Int. Cl.
*G01N 21/31* (2006.01)

(52) U.S. Cl.
CPC ..... *G01N 21/31* (2013.01); *G01N 2201/0633* (2013.01); *G01N 2201/0636* (2013.01);
(Continued)

(58) Field of Classification Search
CPC ............. G01N 33/5005; G01N 33/543; G01N 33/5432; G01N 33/60; G01N 30/461; G01N 33/54373; G01N 33/579; G01N 2035/00475; G01N 35/10; G01N 2021/772; G01N 21/45; G01N 21/7703; G01N 2021/436; G01N 21/7743; G01N 2400/50; G01N 2021/3125; G01N 21/314; G01N 21/553; G01N 33/1893; G01N 15/00; G01N 15/06; G01N 21/31; G01N 21/82; G01N 2201/06113; G01N 2201/0633; G01N 2201/0636; G01N 2201/0638;
(Continued)

(56) References Cited

U.S. PATENT DOCUMENTS 5,310,657 A * 5/1994 Berzofsky ............ G01N 33/579
435/23
H1775 H * 1/1999 Ligler .......................... 435/7.92
(Continued)

FOREIGN PATENT DOCUMENTS

EP         0173021 B1 *  5/1992
WO    WO-0007008 A1 *  2/2000   ............ G01N 21/553

*Primary Examiner* — Michael P Stafira
(74) *Attorney, Agent, or Firm* — David G. Rosenbaum; Rosenbaum IP, P.C.

(57) ABSTRACT

A pyrogenicity test method and assay of endotoxins allows for rapid and ultrahigh sensitivity testing of parenteral pharmaceuticals or medical devices that contact blood or cerebrospinal fluid by employing a Limulus Amoebocyte Lysate (LAL) assay monitored with a photonic-crystal biosensor. The photonic-crystal biosensor is capable of determining the presence of endotoxins in a test sample by detecting shifts in the resonant condition of an open microcavity affected by the changes in the refractive index of the analyte solutions used.

14 Claims, 4 Drawing Sheets
(4 of 4 Drawing Sheet(s) Filed in Color)

Related U.S. Application Data

(60) Provisional application No. 62/573,535, filed on Oct. 17, 2017.

(52) U.S. Cl.
CPC ........... *G01N 2201/0638* (2013.01); *G01N 2201/06113* (2013.01); *G01N 2201/08* (2013.01)

(58) Field of Classification Search
CPC ......... G01N 2201/08; G01N 2333/165; G01N 33/54306; G01N 33/569; G01N 33/56983; G01B 13/06
See application file for complete search history.

(56) References Cited

U.S. PATENT DOCUMENTS

| | | | | |
|---|---|---|---|---|
| 2004/0241788 A1* | 12/2004 | Wainwright | .......... | B01L 3/5027 435/287.1 |
| 2010/0065732 A1* | 3/2010 | Ye | .......... | G02B 1/005 250/281 |
| 2014/0322819 A1* | 10/2014 | Witte | .......... | G01N 33/54373 422/69 |

\* cited by examiner

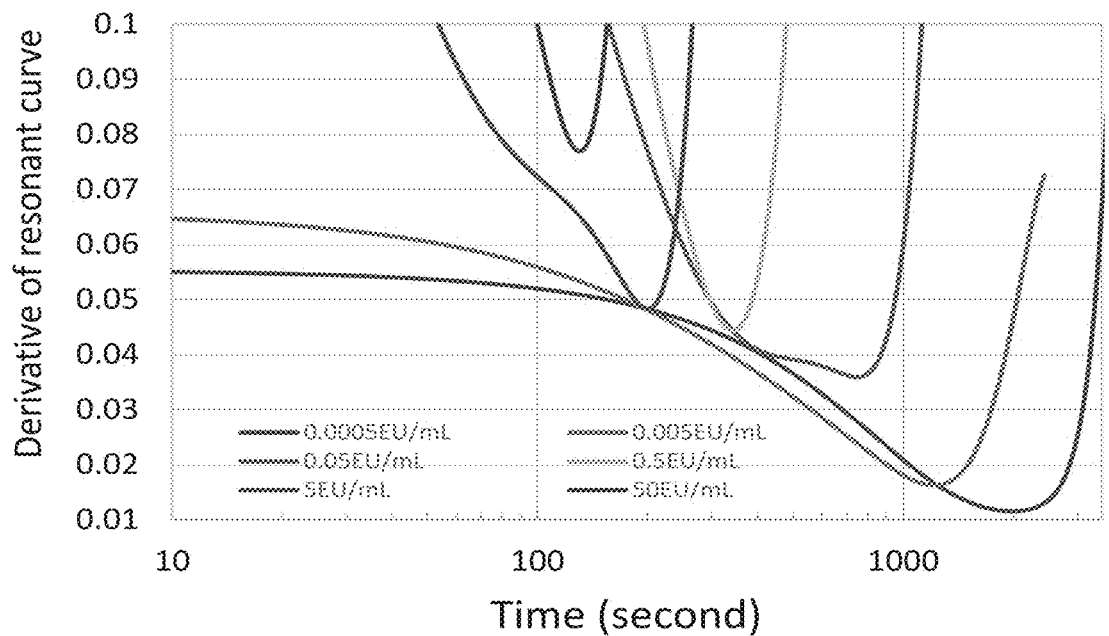
FIG. 5
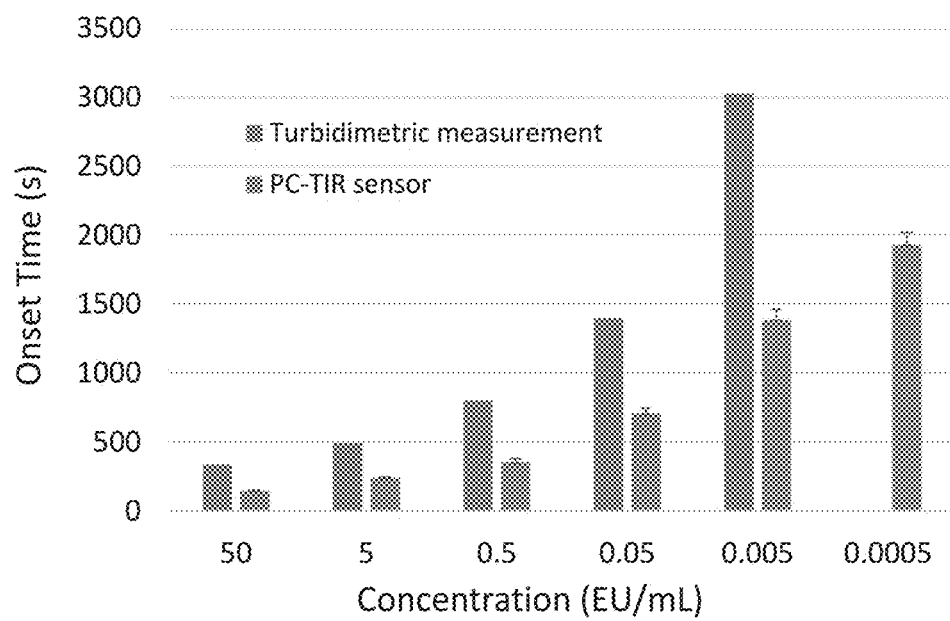
FIG. 6;

ENDOTOXIN TESTING ASSAY AND METHOD OF SAME

CROSS-REFERENCE TO RELATED APPLICATIONS

This application is a continuation-in-part of co-pending U.S. patent application Ser. No. 16/162,261, filed Oct. 16, 2018, which claims priority to U.S. Provisional Ser. No. 62/573,535 filed Oct. 17, 2017, the contents of which are incorporated by reference in their entirety, as if fully restated herein.

BACKGROUND OF THE INVENTION

Almost since its discovery, Limulus Amoebocyte Lysate (LAL) testing has been an important part of the pharmaceutical and food industry quality control toolkit. It allows for in vitro endotoxin testing to judge pyrogenicity of test samples, thus leading to a less expensive and faster test of parenteral pharmaceuticals and medical devices that contact blood or cerebrospinal fluid (Hartung 2015). For more than 30 years, the United States Food and Drug Administration (FDA) has accepted the use of a LAL test for endotoxins in lieu of the rabbit pyrogens test that had been previously employed.

Three different endotoxin testing methods based on LAL assays are currently known and conventionally used: gel-clot, turbidimetric, and chromogenic approaches. Each approach suffers from its own limitations. Thus, there is a growing demand to further increase the LAL test sensitivity, reduce the assay time and minimize interference issues in the assays.

When pharmaceutical products contaminated with pyrogens are injected into the human body, they will give rise to a rapid increase in core body temperature followed by extremely rapid and severe shock, which may cause death in certain situations before the problem is even diagnosed. Therefore, it is critically important to have strict quality control on pharmaceutical products via accurate testing for pyrogenic substances. As the most common source of pyrogen, lipopolysaccharide (LPS) is a naturally occurring endotoxin, coming from a structural component of Gram-negative bacteria cell membranes. LPS is a very stable molecule, and it is difficult to remove from fluids or medications. In fact, the only possible ways to remove the pyrogenic effects of LPS are to either denature it by high heat (250° C. for 30 minutes, 200° C. for 1 hour) or treat with strong acids or bases. Low pressure plasma sterilization, which has brought significant advances to laboratory equipment decontamination, does not adequately reduce the pyrogen load on a surface or a pharmaceutical product (Moisan et al. 2001). In addition to the pharmaceutical industry, detection of endotoxin is also important for the food industry. A 2010 study by the World Health Organization (WHO) revealed that worldwide, there were 351,000 deaths and 582 million cases of food-borne diseases. Of those deaths, 89,000 were caused by two gram-negative bacterial strains, E. coli and Salmonella. Proper test of industrialized food productions for these gram-negative bacteria can minimize the likelihood of contamination and therefore save lives.

LAL endotoxin testing is approved for testing drugs, products and medical devices that come in contact with the blood or cerebrospinal fluid. It is one of the few methods approved by the United States Pharmacopeia and FDA as an acceptable endotoxin testing strategy for oral and injectable medications, as well as implantable devices such as hip replacements, artificial hearts, and man-made ligaments (Taylor 2011). LAL testing has also been employed in a wide variety of studies: testing bacterial growth in Glaciers (Barnett et al. 2012), testing for the presence of pyrogens in nanoparticle fluids (Smulders et al. 2012), verifying safe work environments in ranching and farming (Basinas et al. 2015), and observing that there are endotoxin and (1→3)-β-D-glucan (a component of fungal cell walls) fluctuations with each season (Hwang et al. 2014).

The most important use of the LAL test, to date, is the testing of pharmaceutical contamination by gram-negative bacteria. LAL is an aqueous extract of blood cells (amoebocytes) from horseshoe crabs, which reacts with bacterial endotoxin or lipopolysaccharide (LPS) and results in a semi-solid mass (coagulation) due to a clotting factor contained in LAL. This reaction is the basis of the three conventional LAL test methods, i.e., gel-clot, turbidimetric, and chromogenic approaches. LAL testing based on a gel clot method may give a qualitative result on bacterial endotoxin. The LAL gel clot reaction is a multi-step enzymatic reaction which is initiated by the addition of the fluid of interest into the LAL assay solution in a 1:1 ratio. The endotoxin which may be in the fluid of interest then binds to Factor C reagent (it has also been shown that the endotoxin binds to both Factor C and B initially)(Kobayashi et al. 2015) which then activates Factor B, which then activates the proclotting enzyme and cleaves the coagulogen protein, resulting in the gelation of the mixed solution. The gel clot assay is run in a tube containing a testing solution mixed with LAL reagents. After a one-hour incubation period at 37° C., the tube is flipped upside down. A firm clot that stays in the bottom of the tube indicates the presence of endotoxin, whereas the result is negative for endotoxin if liquid flows down the side of the tube.

In addition to the gel clot test, there are two quantitative, kinetic LAL assays commercially available. The turbidimetric assay uses the same enzymatic cascade as the gel clot test, but adds a turbidity scanner to detect the change in scattered light over the whole reaction sequence, rather than only at the end-point. A test sample is first mixed with LAL reagents and the change in its turbidity with time is then monitored. If endotoxin is present in the sample, the solution becomes cloudy or turbid and the time required for the change in turbidity is inversely proportional to the amount of endotoxin present. The other kinetic assay is termed a chromogenic test, where the manufacturer switches the coagulogen in the final step of the enzymatic cascade with a chromogenic substrate. A test sample is mixed with LAL reagents and the solution becomes yellow in the presence of endotoxin due to the process of cleaving the chromogenic substrate by the activated clotting enzyme. Each of these conventional LAL test methodologies have limited detection sensitivity and speed and are not suitable for samples containing certain inhibitors.

Current LAL assays all have their limitations in detection sensitivity, with the best commercial LAL assay sensitivity of 0.005 EU/mL (Endotoxin Units/milliliter), which equates to 0.0005 ng/mL to 0.001 ng/mL for most bacterial endotoxins (Kobayashi et al. 2015). The current approaches for LAL test are also time consuming, with a typical assay time of one hour. In addition to the limitations in detection sensitivity and speed, another major limiting factor of the LAL test is that it is a protease reaction. Protease inhibitors, anti-coagulation molecules (blood thinners), and LPS sequestration compounds (high-density lipoprotein, albumin, heparin, anti-endotoxin antibodies, bacterial permeability increasing protein, and EDTA) can greatly impact the accuracy of conventional LAL assays.

LAL pyrogen testing fills a sizeable need in today's world (Hartung 2015). The costs of endotoxin testing have been estimated by Markets-and-Markets to be over $823 million in 2019, with a Compound Annual Growth Rate of 12.23% for the foreseeable future (Hartung 2015).

The detection of LPS by the LAL assay is a proxy for how the human body reacts to pyrogens. The horseshoe crab's immune response causes gelation of its blood, but the immune response in humans is inflammation and fever. Because of the inherent complexity of the human body's reaction to a specific molecule or class of molecules, testing for the presence of the chemical makeup of that molecule (i.e. through Gas Chromatograph tests) often leads to false positives or false negatives (Saraf et al. 1997). Even the LAL test itself is not a foolproof way of testing for pyrogenicity in the human body, as the LAL recognition of certain classes of LPS is much stronger than it would be in the human body. Additionally, humans have a pyrogenic reaction to some types of gram positive bacteria, and the LAL test does not react to these (Hartung 2015; Saraf et al. 1997). Even with its limitations, the LAL test is the gold standard for testing for pyrogenicity. It has been used to test a variety of conditions, such as Sepsis treatments (Silverman and Ostro 1999), refining root canal drug delivery strategies (de Oliveira et al. 2012; Marinho et al. 2015), root canal procedure strategies (Sousa et al. 2014), and early indicators of intestinal membrane breakdown in Dengue Fever patients (van de Weg et al. 2012). Due to the limitations of the current LAL test, as well as the large market share of endotoxin testing, refinements of pyrogen tests are constantly being made, including using Quartz sensors (Chalupniak et al. 2014; Liu et al. 2017); electrochemical feedback sensors (Inoue et al. 2012); nanoparticle suspensions (Li et al. 2015); piezoelectric sensors (Muramatsu et al. 1988); and SPR sensors (Su and Ding 2015). In addition, alternative pyrogen test compounds are constantly being engineered, such as the beta glucan only test, GLUCATELL (Obayashi et al. 1995), the Monoclonal Antibody Test (MAT) (Hartung 2015; Sander et al. 2008), recombinant Factor C (Barnett et al. 2012), and nano-molecular imprinted polymers (MIP) (Su and Ding 2015). However, each has inherent problems that result in them not being as sensitive or specific as the LAL test.

The present invention attempts to solve these problems as well as others.

SUMMARY OF THE INVENTION

In accordance with the present invention there is provided a new approach to enhance endotoxin testing and avoid the both the sensitivity and test time limitations of conventional LAL testing methodologies. The present invention provides both a system and method based upon a photonic-crystal biosensor optimized for endotoxin testing. When employing the inventive system and method, endotoxin testing sensitivity has been increased 10 fold over the conventional testing methodologies and the testing duration has been reduced by at least 50 percent over the conventional testing methodologies.

Another aspect of the invention is that the sensitivity increase and assay time reduction of the present system and method may be conducted with a minimum amount of LAL reagents, as little as 5 microliters.

Different from the conventional methodologies, the present invention employs a photonic crystal-total internal reflection (PC-TIR) biosensor for LAL testing. The PC-TIR biosensor allows the inventive system to achieve rapid and ultrasensitive assay results even in the presence of certain inhibitors. The LAL assays with a PC-TIR biosensor is based on the detection of the refractive index (RI) of a test solution, as the refractive index changes during the LAL assay in the presence of endotoxin. The inventive detection mechanism of quantifying endotoxin concentrations via monitoring the changes in the refractive index of the analyte solution reacting with LAL reagents is fundamentally different from the methods currently used in the industry, namely, gel-clot, turbidimetric, and chromogenic approaches.

The PC-TIR biosensor used possesses a unique open optical microcavity. A conventional optical microcavity may result in a sharp resonant condition by having a cavity layer sandwiched by two pieces of photonic crystal (PC) structures. However, this conventional, closed configuration is not suitable for biosensing as it is very difficult to place analyte solutions at the sensing layer (cavity layer). In contrast, the present invention employs an open microcavity structure by splitting the cavity layer through the middle and employing only half of the structure in a total internal reflection (TIR) configuration. There is a mirror image of the PC structure due to TIR. A microcavity can therefore still be formed between the PC structure and its mirror image. This unique configuration forms a PC-TIR biosensor with an open sensing surface, which allows the biosensor directly exposed to the analyte solutions for real-time bioassays. A sharp resonant dip (about 1 nm) can be achieved with a PC-TIR biosensor, which facilitates rapid and sensitive LAL assays by accurately monitoring the change in the sharp resonant condition of the open microcavity affected by the changes in the refractive index of the analyte solutions.

BRIEF DESCRIPTION OF THE DRAWINGS

The patent or application contains at least one drawing executed in color. Copies of this patent or patent application publication with color drawing(s) will be provided by the Office upon request and payment of the necessary fee

FIG. 5 are derivatives of time-dependent curves of resonant peak positions, with the time corresponding to the minimum of each curve determining the onset time of the coagulation process of the LAL reaction to endotoxins which increases with decreasing endotoxin concentrations.

FIG. 6 is a graph comparing onset times between the inventive PC-TIR biosensor LAL assay system measure-

DETAILED DESCRIPTION OF THE PREFERRED EMBODIMENTS

Figure 1:
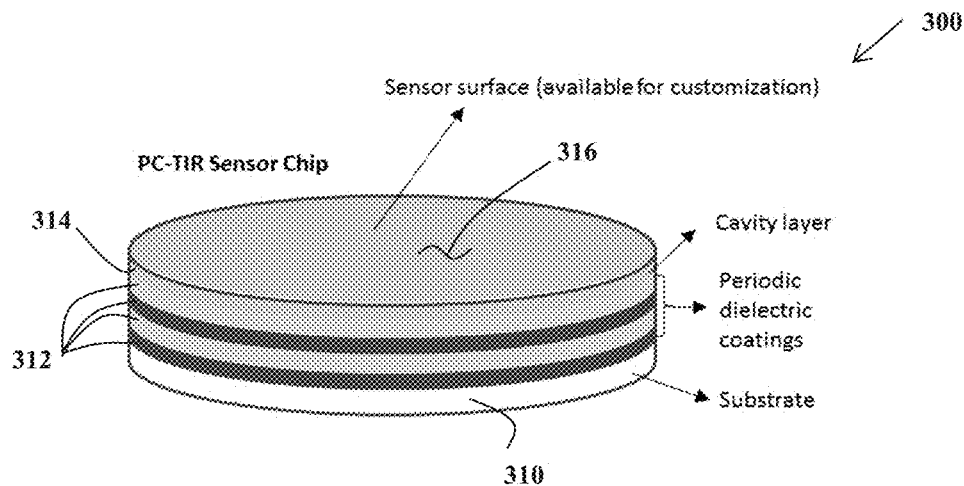
FIG. 1 is a schematic of the PC-TIR sensor for LAL assays.

For purposes of clarity, the following terms used in this patent application will have the following meanings:

The terminology used herein is for the purpose of describing example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the order discussed or illustrated, unless specifically identified as an order of performance. It is also to be understood that additional or alternative steps may be employed.

When an element or layer is referred to as being "on," "engaged," "connected," or "coupled" to or with another element, it may be directly on, engaged, connected or coupled to the other element or layer, or intervening elements or layers may be present. In contrast, when an element is referred to as being "directly on," "directly engaged to," "directly connected to," or "directly coupled to" or with another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below", or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

"Substantially" is intended to mean a quantity, property, or value that is present to a great or significant extent and less than, more than or equal to total. For example, "substantially vertical" may be less than, greater than, or equal to completely vertical.

"About" is intended to mean a quantity, property, or value that is present at ±10%. Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range, including endpoints given for the ranges.

Recitation of ranges of values herein are merely intended to serve as a shorthand method of referring individually to each separate value falling within the recited range, unless otherwise indicated herein, and each separate value is incorporated into the specification as if it were individually recited herein.

References to "embodiment" or "variant", e.g., "one embodiment," "an embodiment," "example embodiment," "various embodiments," etc., may indicate that the embodiment(s) or variant(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment or variant, although they may.

As used herein the term "method" refers to manners, means, techniques and procedures for accomplishing a given task including, but not limited to, those manners, means, techniques and procedures either known to, or readily developed from known manners, means, techniques and procedures by practitioners in the relevant art. Unless otherwise expressed, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used in this application the term "layer" is intended to mean a substantially uniform material limited by interfaces between it and adjacent other layers, substrate, or environment.

This detailed description of exemplary embodiments makes reference to the accompanying drawings, which show exemplary embodiments by way of illustration. While these exemplary embodiments are described in sufficient detail to enable those skilled in the art to practice the disclosure, it should be understood that other embodiments may be realized and that logical changes and adaptations in design and construction may be made in accordance with this disclosure and the teachings herein without departing from the spirit and scope of the disclosure. Thus, the detailed description herein is presented for purposes of illustration only and not for purposes of limitation.

Biosensor Chip Preparation

In accordance with the best mode contemplated for the present invention, the PC-TIR biosensor employed in the present invention is an open optical microcavity and is based upon the PC-TIR biosensor described in U.S. Pat. No. 7,639,362 ('362 Patent), which is herein incorporated by reference in its entirety. Different from the approach taken in the '362 Patent or in previous studies (e.g., Guo, Y., Ye, J. Y., Divin, C., Thomas, T. P., Myc, A., Bersano-Begey, T. F., Baker, J. J. R. & Norris, T. B. Real-Time Biomolecular Binding Detection Using a Sensitive Photonic Crystal Biosensor. *Anal. Chem.* 82, 5211-5218, (2010); Zhang, B., Dallo, S., Peterson, R., Hussain, S., Weitao, T. & Ye, J. Y. Detection of anthrax lef with DNA-based photonic crystal sensors. *J Biomed Opt* 16, 127006, (2011); Zhang, B., Morales, A. W., Peterson, R., Tang, L. & Ye, J. Y. Label-free detection of cardiac troponin I with a photonic crystal biosensor. *Biosens Bioelectron* 58, 107-113, (2014); Zhang, B., Tamez-Vela, J., Solis, S., Bustamante, B., Peterson, R., Rahman, S., Morales, A., Tang, L. & Ye, J. Y. Detection of Myoglobin with open-cavity and label-free photonic crystal biosensor. *Journal of Medical Engineering*, 808056, (2013); Zhang, B., Wang, B., Morales, A. W., Scudder, J., Bhattacharyya, M. K. & Ye, J. Y. Study of the Interactions of Fusarium virguliforme Toxin FvTox1 with Synthetic Peptides by Molecular Simulations and a Label-Free Biosensor. *Anal Chem* 88, 3024-3030, (2016)), where the PC-TIR sensor was used for molecular binding assays, the present invention relies upon detecting changes in the refractive index of LAL analyte solutions caused by endotoxins. The inventive PC-TIR biosensor was designed based on numerical simulations with a transfer matrix approach and fabricated with electron-beam physical vapor deposition.

As shown in FIG. 1, the inventive PC-TIR biosensor 300 has a plurality of alternating layers 312 of titanium dioxide and silicon dioxide coated on a glass substrate 310. It will be understood by those skilled in the art that other suitable coatings may be employed on glass substrate 310 other than titanium dioxide and/or silicon dioxide. In accordance with an illustrative embodiment, each $TiO_2$ layer is about 91 nm in thickness, each $SiO_2$ layer is about 309 nm in thickness and a glass substrate is BK-7 optical glass. A cavity layer 314 was formed above the plurality of alternating layers and was formed with about 374.6 nm of silica and about 13 nm of silicon. The thin silicon layer gives rise to an appropriate level of absorption such that a sharp dip in the reflectance spectrum is introduced at the resonant wavelength of an open optical microcavity or open cavity formed when the PC structure is used in a TIR configuration (Ye et al. 2013; Ye et al. 2009). When the wavelength of a probe light is fixed, i.e., a laser beam rather than a broadband white light source, the change in refractive index can also be quantified by measuring the change in the resonant angle of the sensor. Thus, when the refractive index of the analyte solutions on top of the PC-TIR biosensor surface changes, the resonant wavelength shifts accordingly.

Sample wells, analyte wells or microfluidic channels (410 in FIG. 2) can be attached to or formed in the top surface of the PC-TIR sensor 422 for sample handling, which may be made of silicone or formed using a polydimethylsiloxane (PDMS) replica molding process according to one embodiment. PDMS base and curing agents (SYLGARD184, Dow Corning) were mixed at a ratio of about 10:1. The mixture was degassed in a vacuum chamber for about 10 minutes and then cast on a mold and cured at room temperature. To bind the sample wells with the biosensor chip, the surface of a PC-TIR biosensor chip and the PDMS sample well were first processed with a plasma cleaner (Harrick Plasma) for about 60 seconds, which renders the surface hydrophilic. The silanol (SiOH) groups created on the surface form bridging Si—O—Si bond when the oxidized PDMS surface was placed in contact with the biosensor chip surface, creating an irreversible seal. For experimental purposes, three sample wells 410 were sealed on the surface of the PC-TIR sensor 422. The PC-TIR biosensor chips together with the sample wells were baked at 200° C. for 1 hour before usage to remove any possible contaminations.

Biosensor Apparatus

Figure 2:
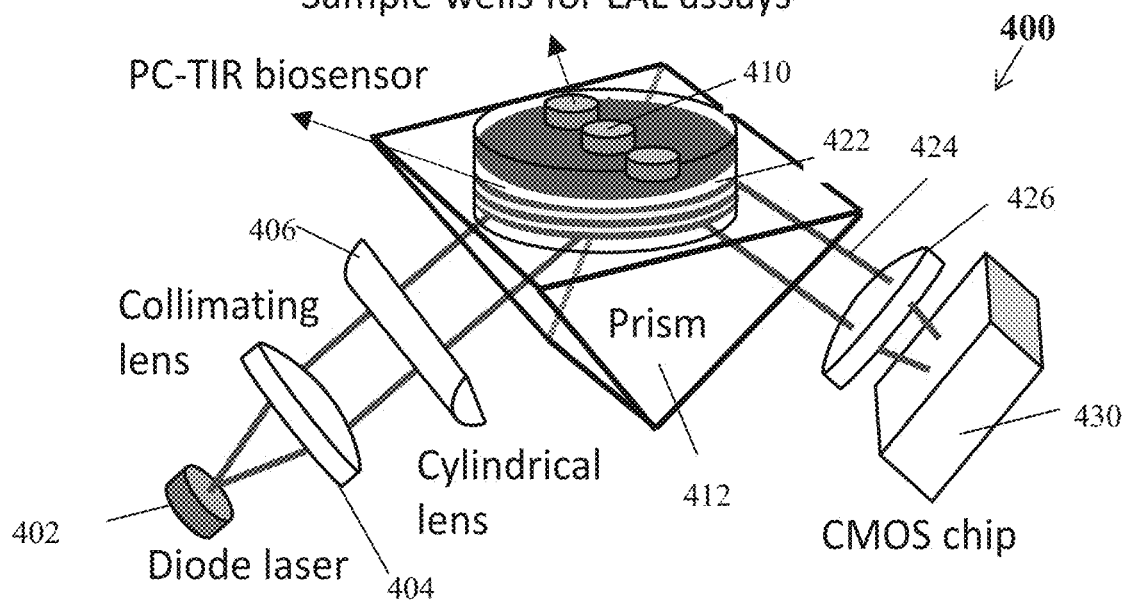
FIG. 2 is a schematic of the inventive PC-TIR sensor-based LAL assay system in an angular detection mode.

The inventive LAL assay system 400 was utilized in an angular detection mode, as shown in FIG. 2. For this embodiment, a light source, such as a diode laser 402 with an emission wavelength at 635 nm, was first collimated through a collimating lens 404 and then focused using a cylindrical lens 406 into a line across the sample wells 410 on the surface of the PC-TIR sensor 422. The PC-TIR sensor 422 was coupled with a BK7 glass prism 412 using refractive-index matching fluid (not shown). Three sample wells 410, each made of silicone, were sealed on the surface of the PC-TIR sensor 422 to contain the LAL reagents and analyte solutions. An output beam 424 reflected from the PC-TIR sensor 422 was collected with a lens 426 and projected onto a CMOS imaging chip 430. Dark lines that correspond to the resonant angle of the sensor were recorded on the images. The positions of the resonant lines on the images, determined by the refractive indices of the samples, were analyzed with a MATLAB program. The entire system 400 was housed in a chamber with a temperature set at 37° C.

Limulus Amoebocyte Lysate (LAL) and Endotoxin Preparation

In one embodiment, an LAL reagent KTA2 (from Charles River Laboratories with a marked sensitivity of 0.005 EU/mL) was used. KTA2 is a kinetic turbidimetric reagent. The directions for proper rehydration and preparation included in the LAL reagent package were followed. The control standard endotoxin (CSE) was also purchased from Charles River Laboratories. Included in the CSE package was the Certificate of Analysis, which specifies the potency (pyrogenicity) of the dehydrated endotoxin in EU/mg. The CSE was reconstituted with LAL Reagent Water (LRW) and vortexed vigorously for 5 minutes before further dilutions. Serial dilutions were made to prepared the test solutions containing 50, 5, 0.5, 0.05, 0.005, 0.0005 EU/mL endotoxin, respectively.

Measurement Procedure

After the appropriate dilutions of CSE were made and LAL reagents were rehydrated, the baked biosensor was placed on an equilateral prism with index matching fluid as shown in FIG. 2. A small amount of LAL reagent (6 µL) was then mixed with 6-µL CSE having a concentration ranging from 50 to 0.0005 EU/mL, while another 6-µL LAL reagent was mixed with 6-µL LRW for using as a reference. A portion (10-µL) of the mixture was taken and added into a sample well on the PC-TIR sensor. A coverslip was used to cover the sample wells to prevent evaporation.

Figure 3:
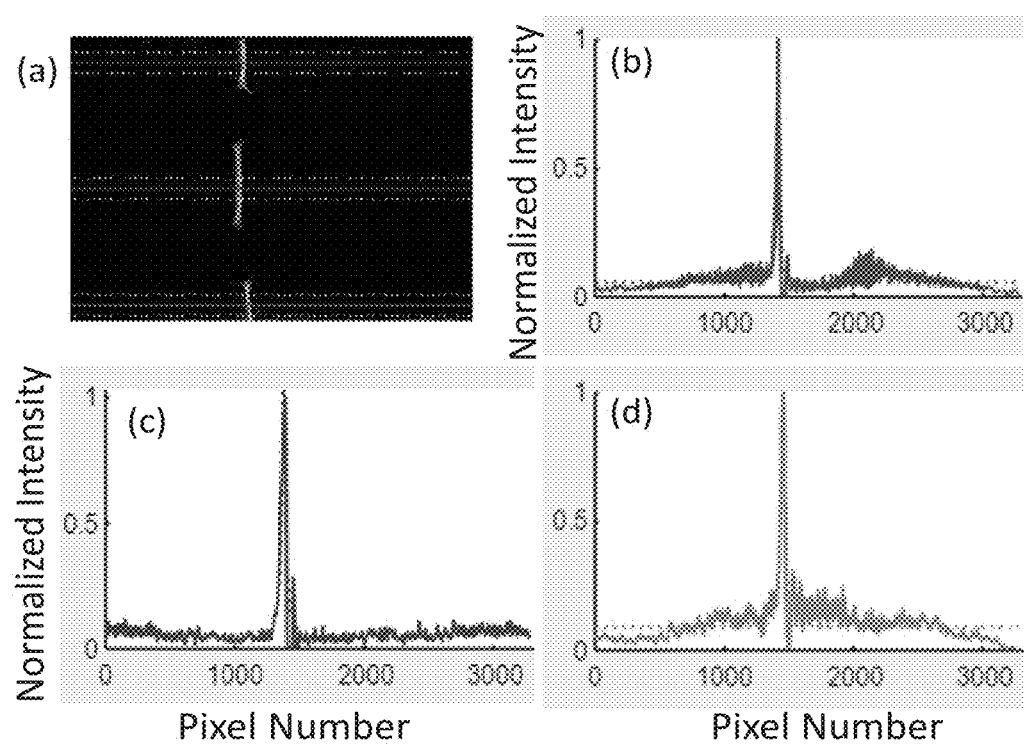
FIG. 3 is a series of four panels with panel (a) being a representative image of the probe laser beam reflected from a PC-TIR sensor showing the position of three lines corresponding the resonant angles of the sensor at three sample wells; panels (b)-(d) are graphs showing the normalized intensity profiles across each resonant line in panel (a), with the reflection angle corresponding to the pixel numbers.
Figure 4:
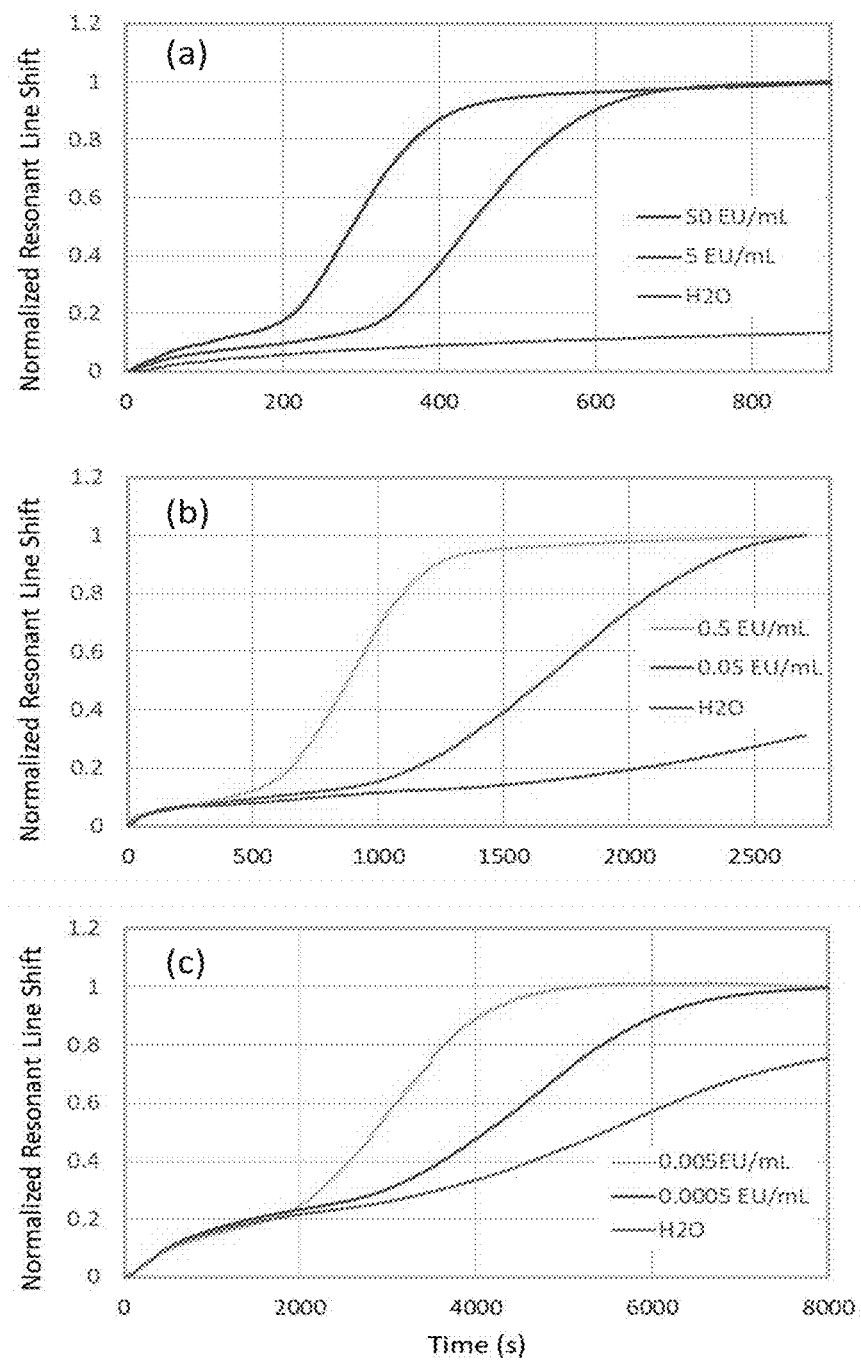
FIG. 4 is a series of three graphs showing resonant curves of the time dependence of the resonant line shifts of the PC-TIR sensor for samples with different concentrations of endotoxins; panel (a) graphs 50 and 5 EU/mL endotoxin concentrations; panel (b) graphs 0.5 and 0.05 EU/mL endotoxin concentrations; panel (c) graphs 0.005 and 0.0005 EU/mL endotoxin concentrations. Water controls were used in each experiment.

The probe laser beam focused by a cylindrical lens formed a line across three sample wells on the sensor surface simultaneously. The reflected beam of the probe laser from the sensor containing a range of different angles was projected onto an imaging chip to measure the resonant angle of the sensor. A dark line appeared on the image indicating the resonant angle determined by the refractive index of the analyte solution in the corresponding sample well. The MATLAB code and computer processed the images in real time. A background image was used to subtract the image with the dark lines, resulting in an image with three short sections of bright lines (FIG. 3, panel a) corresponding to the samples in each of the three sample wells on the PC-TIR sensor surface. The intensity profile of each bright line was obtained from the processed image (FIG. 3, panels b-d) and fitted with a Lorentzian function to determine the peak position. The images were taken every three seconds and processed to continuously monitor the change of the peak positions. The peak position was observed shifting with the coagulation process of the sample due to the interactions of the LAL reagent with the endotoxin (FIG. 4). After the assay, the sample wells and the sensor chip were cleaned first with acetone, and then with deionized water, dried with compressed air to assure no fluid solution remains on the sensor surface. In order to reuse the biosensor, the cleaned PC-TIR sensor chips were baked at 200° C. on a hot plate or oven for at least one hour in an aluminum enclosure, to ensure even heat transfer, and to restrict room air contamination.

Sample measurements were replicated five times for each CSE concentration to make statistical analysis possible. Standard errors were calculated and plotted as error bars showing the measurement results. Standard deviations were also calculated. Because each data point consisted of the average of about 10 spectral samples, the standard error was selected as the appropriate error bar in figures showing run results. Standard deviation and the coefficient of variation were also calculated using Excel.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in degrees Centigrade or is at ambient temperature, and pressure is at or near atmospheric.

Results

In previous studies PC-TIR sensors were used for molecular binding assays ranging from well-studied coupling agents to small molecule binding and nucleic acid and cardiac biomarker detection (Guo et al. 2010; Guo et al. 2008; Zhang et al. 2011; Zhang et al. 2014; Zhang et al. 2013; Zhang et al. 2016, supra). In contrast, for the first time, the present invention utilizes the PC-TIR biosensor to monitor the changes in the refractive index of LAL analyte solutions, which sensitively reflects the amount of endotoxin in the test samples. FIG. 3 (panels b-d) shows representative intensity profiles of three resonant lines of a PC-TIR biosensor at a certain time point when analyte solutions were added on the biosensor surface. The sharp resonant line shifts with time while the LAL responds to the endotoxin.

As shown in FIG. 3 panel (a), the image of the probe laser beam reflected from the PC-TIR sensor displays a short line corresponding to the resonant angle of the sensor at each of three sample wells. Panels (b)-(d) are each the normalized intensity profile across each resonant line from FIG. 3 panel (a), with the pixel numbers corresponding to the reflection angle of the laser light. The peak position of each resonant line was continuously monitored by taking the images every three seconds throughout the LAL assay process for each sample. A Lorentzian function was used to fit each curve in order to precisely determine the peak position as it shifts during the LAL reaction process due to the change of the local refractive index caused by endotoxins. By fitting the curve rather than simply picking the highest point of the curve, a more accurate value of the resonant angle is obtained. The sharp resonant condition of the PC-TIR sensor allows for precise determination of the peak position, thus leading to accurate quantification of the refractive index changes related to the endotoxin concentration.

The time dependence of the peak positions obtained from fitting the curves for six different concentrations of endotoxin ranging from 0.0005 EU/ml to 50 EU/ml as well as the control sample is shown in FIG. 4 panels (a)-(c). It can be seen that the curve from each sample slowly increases with time initially and at certain time point the curve starts to shift up at a much higher rate before it reaches a plateau. The time point for the rapid increase corresponds to the onset time of the coagulation process of the LAL reactions with the endotoxin. Different onset times are observed for different endotoxin concentrations. FIG. 4, panel (c) shows that even the curve for the negative control sample eventually started to shift up at an increased rate in a longer time scale. This shift may be attributed to a possible minute amount of endotoxin in the water used in this measurement. Although the depyrogenated LRW) from Charles River was specifically chosen to minimize any possible contaminations, it is still possible that an extremely low level (<0.0005 EU/mL) of endotoxin may exist in the sample, as the LRW is only guaranteed to have an endotoxin level less than 0.001 EU/mL. It is, therefore, likely that the detection limit (0.0005 EU/mL) observed in this experiment is actually due to the limitation of the control sample rather than the detection approach itself. The detection approach may allow distinguishing endotoxins with an even higher sensitivity where a control having a more stable curve is obtained. The significant improvement in detection sensitivity is, at least in part, due to the PC-TIR sensor's capability for ultrasensitive measurements of the refractive index changes in the analyte solutions caused by LAL reactions to the minute amount of endotoxin.

To illustrate the fast response of the PC-TIR sensor to LAL assays, the derivative of the time-dependent curves of the resonant peak positions was used to determine the onset time of the coagulation process of the LAL reaction to endotoxins. The time corresponding to the minimum of each derivation curve in FIG. 5 determines the onset time for the endotoxin concentration used for that measurement, as the shift of the resonant line speeds up after that time point due to the onset of the coagulation process, which causes the increase of the local refractive index. It can be seen in FIG. 5 that the onset time increases with decreasing endotoxin concentration. The average onset time for an endotoxin sample at 50-EU/mL is less than 3 minutes. The average onset time increases to 32 minutes for the lowest endotoxin concentration (0.0005 EU/mL) as measured in the current experiment. Therefore, the onset time is a useful parameter to quantify the endotoxin concentration in the test sample.

When compared to a conventional turbidimetric LAL assay, i.e., from Charles River Laboratories, the inventive PC-TIR biosensor measurement demonstrated both faster assay times as well as ultrahigh sensitivity. FIG. 6 demonstrates that the onset time for the lowest endotoxin concentration (0.0005 EU/mL) measured with the PC-TIR sensor is faster than the onset time for a sample with even 10 times higher endotoxin concentration (0.005 EU/mL) measured with a conventional turbidimetric approach, although both measurements used the same LAL reagents. There is no data available for the 0.0005-EU/mL endotoxin concentration from Charles River Laboratories, as their turbidimetric approach has a detection sensitivity limited to 0.005 EU/mL. The short assay time for the PC-TIR sensor-based detection may be attributed to the fast response of the change in refractive index due to the onset of the coagulation of the analyte solution. The open microcavity of the PC-TIR sensor has a sharp resonant condition, which is highly sensitive to the local change in the refractive index of a solution in a proximity of several hundreds of nanometers above the sensing surface. The refractive index may start to change immediate after the onset of the coagulation process, before a gel clot is formed. The significantly shortened assay time of the PC-TIR approach compared with the other methods is desired for many industry applications, such as with "in-line" quality control of products.

The data indicate that even the most diluted endotoxin solution used (0.0005 EU/mL) has resulted a curve that is clearly different from the negative control (LAL reagent mixed with water). Based on the average pyrogenicity of the endotoxin, 0.0005 EU/mL equates approximately to 0.00005 ng/mL of endotoxin in the solution, which demonstrates the superior sensitivity of this PC-TIR sensor-based approach over the conventional approaches. Compared to the best sensitivity achieved in the LAL turbidimetric test available from Charles River Laboratories, the sensitivity of the PC-TIR sensor-based approach has showed a 10-fold enhancement over the industry standard.

The inventive system and method demonstrate that an LAL assay that measures the refractive index of a test solution using a photonic crystal biosensor offers significantly enhanced sensitivity together with substantially faster discrimination of positive and negative results. In addition, the PC-TIR biosensor has a simple 1-dimensional (1D) PC structure, which is basically a multi-layered dielectric coating and can be easily fabricated with well-established vacuum deposition techniques. In contrast to 2D or 3D PC structures, the simplicity of the PC-TIR biosensor structure allows for low-cost reproduction, robust performance, and ultrahigh sensitivity assays, which are important factors for potential commercialization of this unique technique for sensitive and rapid LAL assays. The PC-TIR biosensor chips can also be reused as they are robust through a number of heat cycles.

Furthermore, there is promise in testing samples that possibly have confounding variables via extreme dilution due to the fact the LAL assays on a PC-TIR chip have a very high sensitivity. Future research is needed in this area, and a more complete list of confounding molecules can be tested with the PC-TIR chip with the endotoxin standard, blood plasma, and other analytes of interest. A method for binding the LAL proteins to the biosensor surface in conjunction with a microfluidic system may further lead to lower volumes of LAL needed to test solutions for pyrogenicity.

It is shown that the endotoxin test with a PC-TIR sensor in accordance with the described system and method offers a 10-fold enhanced sensitivity compared to commercial standard methods, along with much faster discrimination of positive and negative results. This improvement can be attributed to the unique detection principle that utilizes a new physical parameter—the refractive index of the analyte solution—to monitor the coagulation process during the reaction of the LAL reagent with the analyte solution. In addition to the sensitivity and speed, this approach also allows for using very small amounts of LAL reagents for the assays, with resultant cost savings in the quality control process for pharmaceutical and biotechnology industries, while conserving a most valuable resource; the horseshoe crab.

It has also been found that in addition to using LAL reagents, extracts from LAL reagents that include purified Factor C and/or recombinant Factor C (rFC) may be employed with the present invention. LAL testing may not include protease amplifying steps, thereby necessitating higher sensitivity biosensor be employed. The increased sensitivity of the PC-TIR biosensor in the present system and method, relative to that of conventional LAL assay systems and methods, addresses this need for higher sensitivity.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

We claim:

1. A Limulus Amoebocyte Lysate (LAL) endotoxin assay system comprising an open cavity photonic crystal total internal reflection (PC-TIR) biosensor, the PC-TIR biosensor further comprising a prism, a substrate, at least one dielectric layer on the substrate, at least one analyte well on the at least one dielectric layer, the substrate being coupled to the prism, the endotoxin assay system configured to detect endotoxin in an analyte in the at least one analyte well by monitoring changes in a refractive index of the analyte.

2. The endotoxin assay system of claim 1 further comprising Limulus Amoebocyte Lysate (LAL) reagents added to the at least one analyte well.

3. The endotoxin assay system of claim 1, further comprising a light source generating a light signal that passes through the PC-TIR biosensor to the at least one analyte well and undergoes total-internal reflection in the open cavity of the PC-TIR biosensor.

4. The endotoxin assay system of claim 1, further comprising an optical detector configured to receive transmitted light from the PC-TIR biosensor through the prism.

5. The endotoxin assay system of claim 1, wherein the detection sensitivity of the system is at least less than or equal to 0.0005 EU/ml of the endotoxin.

6. The endotoxin assay system of claim 1, wherein an onset time for changes in the refractive index is determined to quantify the endotoxin concentration in the analyte.

7. The endotoxin assay system of claim 1, further comprising:
 a polarized light source;
 a collimating lens optically coupled to the polarized light source; and
 a first lens receiving light from the collimating lens and passing the light to an optical prism;
 a second lens receiving reflected light from the optical prism and focusing the reflected light onto an imaging chip.

8. The endotoxin assay system of claim 7 wherein an optical fiber is used to optically couple the polarized light source.

9. The endotoxin assay system of claim 1, wherein the PC-TIR biosensor further comprises a plurality of microchannels or wells on a surface thereof.

10. The endotoxin assay system of claim 9, further comprising:
 a lens configured to focus the polarized laser light beam into a line crossing at least one of the plurality of microchannels or wells on the surface of the PC-TIR biosensor; and
 an imaging device capable of imaging the reflected laser light beam to create an image, the image having a plurality of sections corresponding to a resonant angle of the laser light beam.

11. An endotoxin assay method comprising the steps of providing an analyte sample suspected of containing an endotoxin from lipopolysaccharide cell wall component of Gram-negative bacteria in an analyte; adding the analyte sample to at least one sample well optically coupled to and interfacing with a reflecting surface of a total internal reflection open cavity photonic crystal biosensor optically coupled to an optical prism; adding Limulus Amoebocyte Lysate (LAL) reagent to the analyte sample; exposing the analyte sample in the at least one sample well to a focused probe laser signal across the total internal reflection open cavity photonic crystal biosensor; reflecting an output beam from the photonic crystal biosensor through the optical prism; imaging the output beam; and monitoring changes in a refractive index of the analyte sample.

12. The endotoxin assay method of claim 11, further comprising the step of collimating the laser light prior to the step of exposing the analyte sample to a focused laser signal.

13. The endotoxin assay method of claim 11, further comprising the step of measuring statistically significant shifts in the resonant condition of the biosensor after starting the LAL assay.

14. The endotoxin assay method of claim 11, wherein the reagent selected comprises Factor C or recombinant Factor C.

* * * * *